(12) United States Patent
Maruta et al.

(10) Patent No.: US 9,322,818 B2
(45) Date of Patent: Apr. 26, 2016

(54) FUEL PHYSICAL PROPERTY DETERMINATION METHOD AND FUEL PHYSICAL PROPERTY DETERMINATION DEVICE

(75) Inventors: Kaoru Maruta, Sendai (JP); Hisashi Nakamura, Sendai (JP); Soichiro Kato, Tokyo (JP); Kunio Matsui, Chiryu (JP); Akira Sase, Tokyo (JP); Tsuyoshi Saura, Okazaki (JP)

(73) Assignees: TOHOKU UNIVERSITY (JP); IHI CORPORATION (JP); IHI INSPECTION & INSTRUMENTATION CO., LTD. (JP)

( * ) Notice: Subject to any disclaimer, the term of this patent is extended or adjusted under 35 U.S.C. 154(b) by 294 days.

(21) Appl. No.: 14/003,303

(22) PCT Filed: Mar. 7, 2012

(86) PCT No.: PCT/JP2012/055794
§ 371 (c)(1),
(2), (4) Date: Sep. 5, 2013

(87) PCT Pub. No.: WO2012/121281
PCT Pub. Date: Sep. 13, 2012

(65) Prior Publication Data
US 2013/0340502 A1    Dec. 26, 2013

(30) Foreign Application Priority Data
Mar. 7, 2011    (JP) .................................. 2011-049523

(51) Int. Cl.
*G01N 33/28*    (2006.01)
(52) U.S. Cl.
CPC ............ *G01N 33/28* (2013.01); *G01N 33/2829* (2013.01)

(58) Field of Classification Search
CPC ... G01N 33/2829; G01N 25/50; G01N 25/52; G01N 33/28; G01N 21/3504; G01N 25/22; G01N 31/005
USPC ........................................................ 73/35.02
See application file for complete search history.

(56) References Cited

U.S. PATENT DOCUMENTS 3,738,808 A      6/1973  Cunningham et al.
4,057,393 A  *  11/1977  Budzak ................ G01N 31/005
                                                        422/78

(Continued)

FOREIGN PATENT DOCUMENTS

JP    02-216439    8/1990
JP    2008-223567  9/2008

(Continued)

OTHER PUBLICATIONS

Office Action dated Jul. 25, 2014 issued in corresponding Korean Patent Application No. 10-2013-7023475 with English translation.

(Continued)

*Primary Examiner* — Freddie Kirkland, III
(74) *Attorney, Agent, or Firm* — Ostrolenk Faber LLP

(57) ABSTRACT

The fuel physical property determination method relating to the first aspect of the present invention includes: a test fuel flame-imaging step of obtaining imaging data by imaging flames formed by supplying a pre-mixed gas containing a test fuel and an oxidant agent, to a test tube in which an internal flow path thereof has a diameter set smaller than a flame-quenching distance at normal temperature; and a physical property determination step of determining a physical property of the test fuel by comparing the imaging data obtained in the test fuel flame-imaging step and imaging data obtained by imaging flames ignited by supplying a pre-mixed gas containing a standard-mixed fuel and an oxidant agent, to the test tube, the standard-mixed fuel having a known physical property.

18 Claims, 4 Drawing Sheets

(56) References Cited

U.S. PATENT DOCUMENTS

| | | | | |
|---|---|---|---|---|
| 4,220,452 | A * | 9/1980 | Bray | G01N 25/50 422/119 |
| 5,822,058 | A * | 10/1998 | Adler-Golden | G01N 21/359 356/300 |
| 7,248,357 | B2 * | 7/2007 | Servaites | G01N 21/359 250/205 |
| 7,511,802 | B2 * | 3/2009 | Smith | G01N 21/39 356/326 |
| 7,529,616 | B2 * | 5/2009 | Bizub | G01N 33/2829 701/103 |
| 7,925,449 | B2 * | 4/2011 | Lutnick | G01N 33/2829 702/182 |
| 8,255,168 | B2 * | 8/2012 | Lutnick | G01N 33/2829 702/182 |
| 8,735,820 | B2 * | 5/2014 | Mertens | G01J 3/28 250/338.1 |
| 2007/0239345 | A1 * | 10/2007 | Bizub | G01N 33/2829 701/114 |
| 2008/0201084 | A1 * | 8/2008 | Lutnick | G01N 33/2829 702/23 |
| 2010/0141949 | A1 * | 6/2010 | Bugge | G01N 21/39 356/402 |
| 2012/0295365 | A1 * | 11/2012 | Maruta | G01N 33/2829 436/155 |

FOREIGN PATENT DOCUMENTS

| | | |
|---|---|---|
| JP | 2010-110724 | 5/2010 |
| JP | 2010-112892 | 5/2010 |
| JP | 2011-149739 | 8/2011 |

OTHER PUBLICATIONS

Ankush Bhasin, "Method for determination of octane rating by flame quenching experiments", MS (Master of Science) thesis, University of Iowa (88 pages) (2010).

Akira Yamamoto et al., "Stabilized three-stage oxidation of gaseous *n*-heptane/air mixture in a micro flow reactor with a controlled temperature profile", Science Direct, Proceedings of the Combustion Institute, vol. 33, pp. 3259-3266 (2011).

International Search Report dated May 29, 2012 issued in corresponding International patent application No. PCT/JP2012/055794.

JIS (Japanese Industrial Stadards) K2280 (partial translation).

Mikito Hori, Akira Yamamoto, et al., "Octane-ka Henka ni Taisuru Ondo Bunpu Seigyogata Micro Flow Reactor Nai Weak flame no Oto", Proceedsing of the Japanese symposium on Combustion, Nov. 20, 2010, vol. $48^{th}$, pp. 376 to 377.

Mikito Hori, Akira Yamamoto, Hiroshi Oshibe et al., "Ondo Bunpu Seigyogata Micro Flow Reactor ni Okeru PRF/ Kuki Yokongoki no Chakka Nensho Tokusei", National Heat Transfer Symposium of Japan Koen Ronbushu (CD-ROM), 2010, vol. $47^{th}$, p. ROMBUNNO. B132.

Hisashi Nakamura, et al., "Ondo Bunpu Seigyogata Micro Flow Reactor o Mochiita PRF no Jichakka Tokusei", Proceedings of the Japanese symposium on Combustion, Nov. 18, 2009, vol. $47^{th}$, pp. 234 to 235.

* cited by examiner

FUEL PHYSICAL PROPERTY DETERMINATION METHOD AND FUEL PHYSICAL PROPERTY DETERMINATION DEVICE

CROSS REFERENCE TO RELATED APPLICATIONS

The present application is a 35 U.S.C. §371 National Phase conversion of PCT/JP2012/055794, filed Mar. 7, 2012, which claims benefit of Japanese Application No. 2011-049523, filed Mar. 7, 2011, the disclosure of which is incorporated herein by reference. The PCT International Application was published in Japanese.

TECHNICAL FIELD

The present invention relates to a fuel physical property determination method and a fuel physical property determination device.

Priority is claimed on Japanese Patent Application No. 2011-049523, filed on Mar. 7, 2011, the contents of which are incorporated herein by reference.

BACKGROUND ART

As a measurement showing the physical properties of a fuel, the octane number is provided which is the indicator showing the anti-knock property of the fuel. The octane number of isooctane having a high anti-knock property is 100, and the octane number of normal heptane having a low anti-knock property is 0. The octane number of a fuel is the number corresponding to a volume percent of isooctane in a mixed fuel (standard-mixed fuel) containing isooctane and normal heptane, the anti-knock property of the mixed fuel being set equal to the anti-knock property of the fuel. That is, when the anti-knock property of a fuel is equal to that of a mixed fuel in which the mixture ratio of isooctane is 50% in volume percent, the octane number of the fuel is shown as 50.

There are octane numbers of various types depending on methods or the like to determine them. For example, the research octane number adopted as the indicator in Japan, and the motor octane number adopted as the indicator in Germany are provided as the major octane numbers.

When obtaining the octane number of a fuel having an unknown octane number, the octane number is determined by performing experiments based on the above-described determination methods for the octane number.

Specifically, as shown in Non-Patent Document 1, for the research octane number and the motor octane number, a CFR engine designed exclusively to measure octane number is operated using the above fuel, and the pressure fluctuation features in a combustion chamber in this operation are compared with that in a case of operating the engine using the standard-mixed fuel. Thereby, the above octane number is determined.

The pressure values in the combustion chamber of an internal-combustion engine are changed depending on occurrence or non-occurrence of knocking. Therefore, the occurrence or non-occurrence of knocking is determined by measuring the pressure values in the combustion chamber, and the measurement timings thereof and the measured values are compared between using the fuel as a determination target and using the standard-mixed fuel. Thereby, the above octane number can be determined.

DOCUMENT OF RELATED ART

Patent Document

[Patent Document 1] Japanese Unexamined Patent Application, First Publication No. 2010-112892

Non-Patent Document

[Non-Patent Document 1] JIS (Japanese Industrial Standards) K2280

SUMMARY OF INVENTION

Technical Problem

However, the pressure values in the combustion chamber are changed due to the dirt condition in the combustion chamber of the CFR engine. Therefore, in order to determine an exact octane number, before the experiments to determine the octane number of a fuel are performed, the preliminary experiments to obtain the information of the dirt condition in the combustion chamber have to be performed.

For example, in a case of determining the research octane number, the preliminary experiments are performed in which the CFR engine is operated using an inspection fuel of toluene series and the dirt condition in the combustion chamber is obtained based on this operational status.

Furthermore, the experiments to determine the octane number have to be performed in consideration of the dirt condition in the combustion chamber obtained by the preliminary experiments.

That is, in conventional octane number determination methods, every time the experiments to determine the octane number are performed, the above preliminary experiments have to be performed. As a result, the operations in the above experiments and the above preliminary experiments become complicated.

Conventionally, in a case of determining the octane number which is not limited to the research octane number or the motor octane number, an internal-combustion engine is actually operated using each of a target fuel and the standard-mixed fuel, and the octane number is determined based on these operational statuses. That is, since the measured values are changed depending on the condition in the combustion chamber or the like of the internal-combustion engine, an exact octane number is not easily determined.

In the conventional octane number determination methods, when determining the octane number depending on the actual usage environment for the internal-combustion engine, this environment has to be created in each determination, and the octane number has to be determined by performing the above-described experiments in this environment. For example, when determining the octane number depending on the temperature of a fuel, the experiments have to be performed in a state in which the temperature of the fuel is changed actually.

Therefore, in the conventional octane number determination methods, the internal-combustion engine has to be prepared in each determination, a facility to create the above environment has to be arranged, and a plurality of complex experiments have to be performed. As a result, the operations in the above experiments become complicated.

In addition, in order to determine physical properties of a fuel which are not limited to the octane number, a plurality of experiments including complex operations have to be performed.

On the other hand, a method is proposed in which parameters (parameters relating to elementary reaction) required for a simulation using a fuel are obtained from temperature distribution in one-dimensional space obtained using a micro flow reactor as shown in Patent Document 1, and the physical properties of the fuel are determined by performing the simulation using the parameters.

According to the above-described physical property determination method, the physical properties of the fuel can be determined in a short time without performing a plurality of complex experiments.

However, in the micro flow reactor used in the above-described conventional method, a temperature gradient is applied to a test tube in the longitudinal direction thereof, the internal flow path of the test tube having a diameter smaller than a flame-quenching distance at normal temperature, and the ignition temperature of a fuel is measured by observing ignition positions of the fuel supplied from one end of the test tube.

Therefore, in the conventional method shown in Patent Document 1, the temperature gradient applied to the test tube in order to measure the ignition temperature has to be measured exactly, and the measuring operations for temperature have to be performed carefully. As a result, the work burden thereof is increased.

A first aspect relating to the present invention has been made in view of the above problems, and aims to shorten the time required to determine physical properties of a fuel by reducing the work burden thereof.

Solution to Problem

The present invention adopts the following configurations as means to solve the above problems.

According to a first aspect of the present invention, a fuel physical property determination method to determine a physical property of a test fuel, the method includes: a test fuel flame-imaging step of obtaining imaging data by imaging flames formed by supplying a pre-mixed gas containing the test fuel and an oxidant agent, to a test tube which includes an internal flow path and in which a temperature distribution is formed; and a physical property determination step of determining the physical property of the test fuel by comparing the imaging data obtained in the test fuel flame-imaging step and imaging data obtained by imaging flames ignited by supplying a pre-mixed gas containing a standard-mixed fuel and an oxidant agent, to the test tube, the standard-mixed fuel having a known physical property.

According to a second aspect of the present invention, in the first aspect, the fuel physical property determination method further includes a standard-mixed fuel flame-imaging step of obtaining the imaging data by imaging flames formed by supplying the pre-mixed gas containing the standard-mixed fuel and the oxidant agent, to the test tube.

According to a third aspect of the present invention, in the second aspect, the standard-mixed fuel flame-imaging step is performed while changing a composition of the standard-mixed fuel, until the imaging data obtained in the test fuel flame-imaging step and the imaging data obtained in the standard-mixed fuel flame-imaging step correspond to each other. In addition, in the physical property determination step, the physical property of the test fuel is determined to be the physical property of the standard-mixed fuel based on the imaging data corresponding to the other.

According to a fourth aspect of the present invention, in the second or third aspect, the pre-mixed gas containing the test fuel and the oxidant agent is supplied to one of disposed test tubes, thereby forming flames. The pre-mixed gas containing the standard-mixed fuel and the oxidant agent is supplied to the other of the test tubes, thereby forming flames. In addition, imaging data is obtained by imaging a plurality of flames at the same time.

According to a fifth aspect of the present invention, in the fourth aspect, the fuel physical property determination method further includes a temperature distribution-forming step of forming the same temperature distribution in the test tubes. In addition, the imaging data of the plurality of flames is obtained in a condition in which temperature distributions in the test tubes are the same in a longitudinal direction thereof.

According to a sixth aspect of the present invention, in any one of the first to fifth aspects, both of an area in which cold flames are expected to be generated and an area in which hot flames are expected to be generated are imaged.

According to a seventh aspect of the present invention, in any one of the first to sixth aspects, the physical property is an octane number.

According to an eighth aspect of the present invention, in any one of the first to sixth aspects, the physical property is a cetane number.

According to a ninth aspect of the present invention, in any one of the first to eighth aspects, the internal flow path of the test tube has a diameter set smaller than a flame-quenching distance at normal temperature.

According to a tenth aspect of the present invention, a fuel physical property determination device to determine a physical property of a test fuel, the device includes: a test tube including an internal flow path; a temperature distribution-forming device to form a temperature distribution in the test tube; a supply device to supply a first pre-mixed gas containing the test fuel and an oxidant agent, to the test tube; an imaging device to obtain first-imaging data by imaging flames formed by supplying the first pre-mixed gas to the test tube; a processing storage device to determine the physical property of the test fuel by comparing the first-imaging data obtained by the imaging device and second-imaging data obtained by imaging flames formed by supplying a second pre-mixed gas containing a standard-mixed fuel and an oxidant agent, to the test tube, the standard-mixed fuel having a known physical property.

According to an eleventh aspect of the present invention, in the tenth aspect, the imaging device is configured to obtain the second-imaging data by imaging flames formed by supplying the second pre-mixed gas containing the standard-mixed fuel and the oxidant agent, to the test tube.

According to a twelfth aspect of the present invention, in the eleventh aspect, the imaging device is configured to repeatedly obtain the first-imaging data and the second-imaging data, until the first-imaging data and the second-imaging data correspond to each other. In addition, the processing storage device is configured to change a composition of the standard-mixed fuel, and to determine that the physical property of the test fuel is the physical property of the standard-mixed fuel when the first-imaging data and the second-imaging data correspond to each other.

According to a thirteenth aspect of the present invention, in the eleventh or twelfth aspect, the test tube includes a first test tube and a second test tube. In addition, the imaging device is configured to obtain the first-imaging data by imaging flames formed by supplying the first pre-mixed gas to the first test tube, and to obtain the second-imaging data by imaging flames formed by supplying the second pre-mixed gas to the second test tube.

According to a fourteenth aspect of the present invention, in the thirteenth aspect, the temperature distribution-forming device is disposed so that temperature distributions in the first and second test tubes are the same in a longitudinal direction thereof.

According to a fifteenth aspect of the present invention, in any one of the tenth to fourteenth aspects, the imaging device is configured to obtain imaging data so as to include both of a first area in which cold flames are expected to be generated and a second area in which hot flames are expected to be generated.

According to a sixteenth aspect of the present invention, in any one of the tenth to fifteenth aspects, the physical property is an octane number.

According to a seventeenth aspect of the present invention, in any one of the tenth to fifteenth aspects, the physical property is a cetane number.

According to a eighteenth aspect of the present invention, in any one of the tenth to seventeenth aspects, the internal flow path of the test tube has a diameter set smaller than a flame-quenching distance at normal temperature.

Effects of Invention

According to the first aspect relating to the present invention, physical properties of a test fuel are determined by comparing imaging data obtained by imaging flames formed using the test fuel and other imaging data obtained by imaging flames formed using a standard-mixed fuel having known physical properties.

Therefore, the physical properties of the test fuel can be determined without obtaining the temperature of a test tube. That is, according to the present invention, the physical properties of the test fuel can be determined without measuring the temperature gradient of the test tube, and it is possible to omit the steps to obtain the temperature gradient of the test tube, which cause an increase in work burden.

Consequently, according to the present invention, it is possible to shorten the time required to determine the physical properties of the fuel, by reducing the work burden.

DESCRIPTION OF EMBODIMENTS

An embodiment of a fuel physical property determination method and a fuel physical property determination device relating to the present invention is described below with reference to the drawings. In addition, in the following drawings, the scale of each member is appropriately changed so that each member has a recognizable size.

First Embodiment

Figure 1:
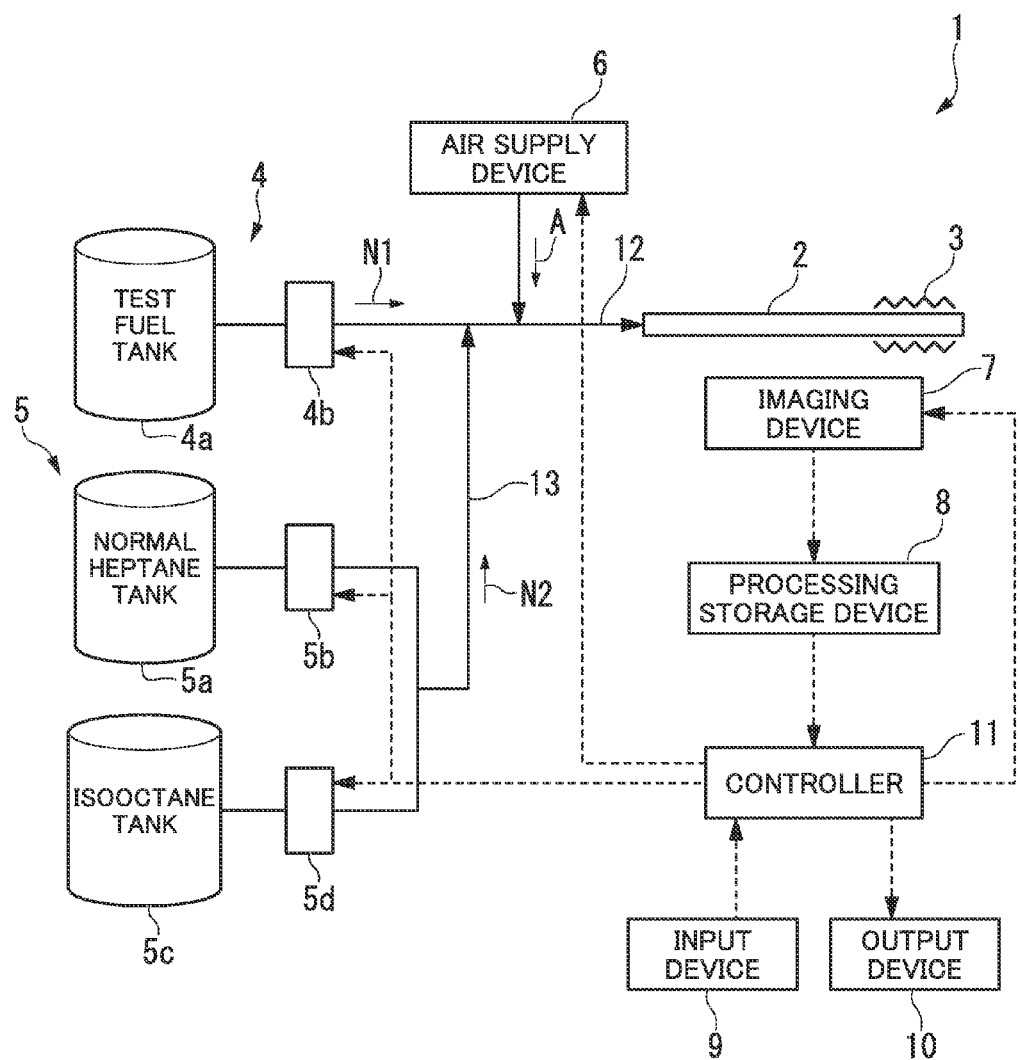
FIG. 1 is a schematic configuration diagram of a fuel physical property determination device in a first embodiment of the present invention.

FIG. 1 is a schematic configuration diagram of a fuel physical property determination device 1 of this embodiment.

The fuel physical property determination device 1 of this embodiment determines the octane number of a test fuel having unknown octane number (physical property). As shown in FIG. 1, the fuel physical property determination device 1 includes a test tube 2, a heater 3 (temperature distribution-forming device), a test fuel supply device 4, a standard-mixed fuel supply device 5, an air supply device 6, an imaging device 7 (imaging means), a processing storage device 8 (processing storage means), an input device 9, an output device 10, and a controller 11.

The test tube 2 is a cylindrical straight tube. The diameter of the internal flow path of the test tube 2 is set smaller than a flame-quenching distance constituting a limit distance in which flames formed in the internal flow path cannot be propagated and are quenched at normal temperature. That is, the diameter of the internal flow path of the test tube 2 is set smaller than a flame-quenching distance at normal temperature.

Pre-mixed gas is supplied to the internal flow path of the test tube 2 from one end of the test tube 2.

The test tube 2 is formed of transparent material so that the imaging device 7 can image flames formed by burning the pre-mixed gas therein. Specifically, the test tube 2 is formed of quartz glass, whereby the test tube 2 can become transparent.

The heater 3 heats the test tube 2, and is disposed so as to surround the end portion of the test tube 2 opposite to the end thereof to which the pre-mixed gas is supplied.

Thereby, a temperature gradient is applied to the test tube 2, the temperature gradient in which the temperature thereof is continuously higher away from the end to which the pre-mixed gas is supplied, to the opposite end thereto. The heater 3 heats the test tube 2 so that the internal temperature of the test tube 2 is greater than or equal to the ignition temperature of the pre-mixed gas at at least part of the test tube in the longitudinal direction thereof, thereby forming temperature distribution.

The test fuel supply device 4 supplies a test fuel N1 having unknown octane number, to a pre-mixed gas supply pipe 12 connected to the one end of the test tube 2. The test fuel supply device 4 includes a test fuel tank 4a storing the test fuel N1 and a flow rate controller 4b to control the flow rate of the test fuel N1 supplied from the test fuel tank 4a to the pre-mixed gas supply pipe 12.

The standard-mixed fuel supply device 5 supplies a standard-mixed fuel N2 having known octane number, to the pre-mixed gas supply pipe 12.

In this embodiment, a mixed gas in which normal heptane and isooctane are mixed is used as the standard-mixed fuel N2.

In this embodiment, the standard-mixed fuel supply device 5 includes a normal heptane tank 5a, a flow rate controller 5b, an isooctane tank 5c, and a flow rate controller 5d.

The normal heptane tank 5a is a tank storing normal heptane to be contained in the standard-mixed fuel N2.

The flow rate controller 5b controls the flow rate of normal heptane supplied from the normal heptane tank 5a to a standard-mixed fuel supply pipe 13. The standard-mixed fuel supply pipe 13 supplies the standard-mixed fuel N2 to the pre-mixed gas supply pipe 12.

The isooctane tank 5c is a tank storing isooctane to be contained in the standard-mixed fuel N2.

The flow rate controller 5d controls the flow rate of isooctane supplied from the isooctane tank 5c to the standard-mixed fuel supply pipe 13.

Each of normal heptane and isooctane is liquid fuel. Therefore, the standard-mixed fuel supply device 5 uses normal heptane and isooctane which have been vaporized inside tanks or the like.

In addition, if the test fuel N1 is liquid fuel, the test fuel supply device 4 also uses the test fuel N1 which has been vaporized inside a tank or the like.

The air supply device 6 supplies the required amount of air A (oxidizing agent) to the pre-mixed gas supply pipe 12.

With regard to the above-required amount of air, the amount of air when the equivalence ratio thereof is 1 corresponds to the amount of air required to completely burn the test fuel N1 or the standard-mixed fuel N2 in the test tube 2. In addition, since the amount of air for the test fuel N1 when the equivalence ratio becomes 1 may not be known beforehand, it is preferable that the amount of air be controlled based on gas analysis or the like in downstream of the fuel physical property determination device 1.

The imaging device 7 images flames formed inside the test tube 2, thereby obtaining imaging data. The imaging device 7 images the test tube 2 and the flames.

At the inside of the test tube 2, cold flames formed by burning the pre-mixed gas at a relatively low temperature, or hot flames formed by burning the pre-mixed gas at a relatively high temperature may be generated.

In addition, the cold flames may not be generated depending on the composition of the pre-mixed gas. In this case, the imaging device 7 images both of the area (first area) in which the cold flames are expected to be generated, and the area (second area) in which the hot flames are expected to be generated.

The imaging device 7 may perform the imaging in the wavelength range of visible light, and may perform the imaging in the wavelength range other than the wavelength range of visible light (for example, the wavelength range of ultraviolet light).

The processing storage device 8 is electrically connected to the imaging device 7. The processing storage device 8 determines the octane number of the test fuel by comparing the imaging data (first-imaging data) obtained by imaging flames formed by supplying the test fuel N1 to the test tube 2 and the imaging data (second-imaging data) obtained by imaging flames formed by supplying the standard-mixed fuel N2 to the test tube 2.

In addition, the processing storage device 8 is configured to include an arithmetic device such as a CPU (Central Processing Unit), and a storage device such as a memory.

The processing storage device 8 in this embodiment determines that the octane number of the test fuel N1 is the octane number of the standard-mixed fuel N2, when the imaging data obtained by imaging flames formed by supplying the test fuel N1 to the test tube 2 corresponds to the imaging data obtained by imaging flames formed by supplying the standard-mixed fuel N2 to the test tube 2. The operations thereof will be described afterward in detail.

The input device 9 is a man-machine interface included in the fuel physical property determination device 1 of this embodiment. The input device 9 is operated by an operator, and inputs signals representing this operation into the controller 11.

The output device 10 visualizes and outputs the processing storage result by the processing storage device 8, or the instructions from the controller 11.

The controller 11 controls all the operations of the fuel physical property determination device 1 of this embodiment. The controller 11 is electrically connected to the test fuel supply device 4, the standard-mixed fuel supply device 5, the air supply device 6, the imaging device 7, the processing storage device 8, the input device 9 and the output device 10.

The controller 11 in this embodiment controls the standard-mixed fuel supply device 5 so that the composition of the standard-mixed fuel is changed gradually, until the imaging data obtained by imaging flames formed by supplying the test fuel N1 to the test tube 2 corresponds to the imaging data obtained by imaging flames formed by supplying the standard-mixed fuel N2 to the test tube 2, in the processing storage device 8. The operations of the fuel physical property determination device will be described afterward in detail.

In the above-described configuration, the processing storage device 8, the input device 9, the output device 10 and the controller 11 are constituted of, for example, a personal computer or a workstation.

In the above-described configuration, a supply device in the present invention is composed of the test fuel supply device 4 and the air supply device 6.

Figure 2:
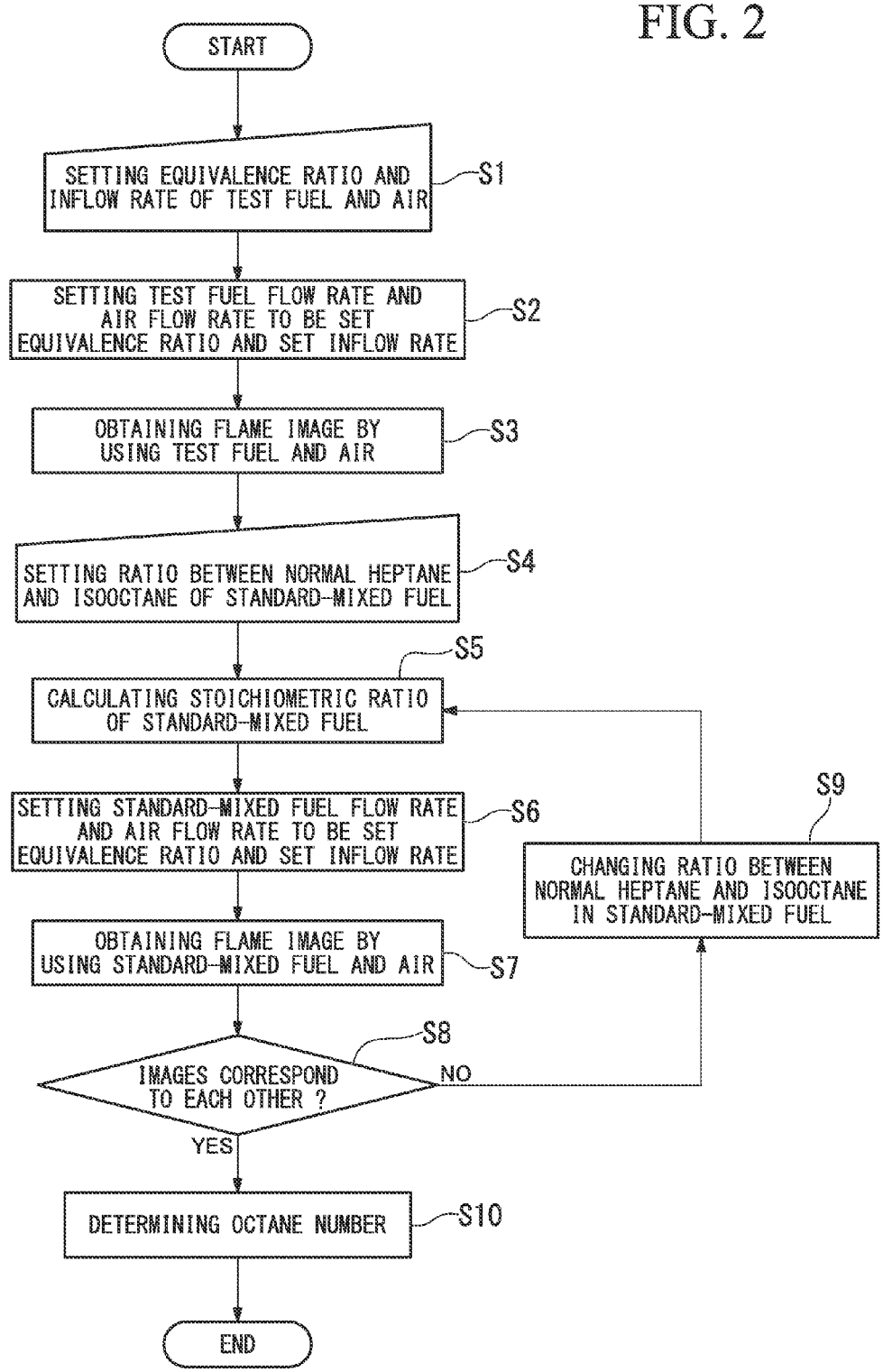
FIG. 2 is a flow diagram to illustrate the operations of the fuel physical property determination device in the first embodiment of the present invention.

Next, the operations (that is, a fuel physical property determination method) of the fuel physical property determination device 1 of this embodiment having the above configuration is described below with reference to the flow diagram in FIG. 2.

In addition, in the following description, the above-described temperature gradient is applied to the test tube 2 by the heater 3.

First, the initial value of the equivalence ratio between the test fuel N1 and the air A, and the initial value of the inflow rate of the pre-mixed gas (first pre-mixed gas) containing the test fuel N1 into the test tube 2 are set (step S1).

Specifically, the controller 11 stores the initial values which have been inputted from the input device 9 in the processing storage device 8, and thereby the setting of the above initial values is performed.

For example, the operator inputs a value obtained by experiments beforehand or a predicted value into the input device 9, thereby setting the equivalence ratio between the test fuel and air.

Since the light emitted from the flames is slight, the imaging device 7 has to be exposed to the light for a long time in order to image the flames. Therefore, it is preferable that the generation position of the flames in the test tube 2 be stable without changing. For example, in Japanese Unexamined Patent Application, First Publication No. 2010-112892 (Patent Document 1), for a test tube having a diameter smaller than or equal to a flame-quenching distance at normal temperature, a method to stabilize the position of flames by reducing the inflow rate of pre-mixed gas is disclosed. In the step S1, the inflow rate of the pre-mixed gas into the test tube 2 is set to a flow rate in which the generation position of the flames in the test tube 2 is stabilized.

Subsequently, the controller 11 lets the test fuel supply device 4 control the supply of the test fuel N1, and lets the air supply device 6 control the supply of the air A, so that actual values become the set equivalence ratio and the set inflow rate which have been set in the step S1 (step S2).

Thereby, the test fuel N1 is supplied from the test fuel supply device 4 to the pre-mixed gas supply pipe 12, and the air A is supplied from the air supply device 6 to the pre-mixed gas supply pipe 12. As a result, the test fuel N1 and the air A are mixed together inside the pre-mixed gas supply pipe 12, thereby composing the pre-mixed gas, and the pre-mixed gas is supplied to the test tube 2.

After the pre-mixed gas is supplied to the test tube 2, the pre-mixed gas is heated and burned inside the test tube 2, thereby forming flames.

Subsequently, the controller 11 lets the imaging device 7 image the flames (step S3). That is, in the step S3, the imaging device 7 images the flames formed using the test fuel N1 and the air A.

In addition, in the step S3, the controller 11 lets the imaging device 7 output the imaging data (first-imaging data) obtained by imaging the flames by the imaging device 7. Furthermore, the controller 11 stores the imaging data outputted from the imaging device 7, in the processing storage device 8.

In the following description, for convenience of description, the imaging data obtained in the step S3 is described as test fuel flame-imaging data.

When the obtaining of the test fuel flame-imaging data in the step S3 is completed, the controller 11 lets the test fuel supply device 4 stop supplying the test fuel N1, and lets the air supply device 6 stop supplying the air A.

Subsequently, the ratio between normal heptane and isooctane in the standard-mixed fuel N2 is set (step S4).

Specifically, the controller 11 stores the instructions denoting the above ratio inputted from the input device 9, in the processing storage device 8, thereby performing the setting.

For example, as the initial value of the ratio between normal heptane and isooctane in the standard-mixed fuel N2, the ratio between normal heptane and isooctane is set to 90%: 10%.

Subsequently, the controller 11 lets the processing storage device 8 calculate the stoichiometric ratio of the standard-mixed fuel based on the ratio set in the step S4 (step S5). In addition, since the standard-mixed fuel is composed of normal heptane and isooctane which have known physical properties, the stoichiometric ratio can be calculated easily.

Subsequently, the controller 11 lets the standard-mixed fuel supply device 5 control the supply of the standard-mixed fuel, and lets the air supply device 6 control the supply of the air A, so that the equivalence ratio and the inflow rate of the pre-mixed gas (second pre-mixed gas) composed of the standard-mixed fuel N2 and the air A correspond to the set equivalence ratio and the set inflow rate which have been set in the step S1 (step S6).

Thereby, the standard-mixed fuel N2 is supplied from the standard-mixed fuel supply device 5 to the pre-mixed gas supply pipe 12, and the air A is supplied from the air supply device 6 to the pre-mixed gas supply pipe 12. As a result, the standard-mixed fuel N2 and the air A are mixed together inside the pre-mixed gas supply pipe 12, thereby composing the pre-mixed gas, and the pre-mixed gas is supplied to the test tube 2.

After the pre-mixed gas is supplied to the test tube 2, the pre-mixed gas is heated and burned inside the test tube 2, thereby forming flames.

Subsequently, the controller 11 lets the imaging device 7 image the flames (step S7). That is, in the step S7, the imaging device 7 images the flames formed using the standard-mixed fuel N2 and the air A. In addition, in the step S7, the controller 11 lets the imaging device 7 output the imaging data (second-imaging data) obtained by imaging the flames by the imaging device 7. Furthermore, the controller 11 stores the imaging data outputted from the imaging device 7, in the processing storage device 8.

In the following description, for convenience of description, the imaging data obtained in the step S7 is described as standard-mixed fuel flame-imaging data.

When the obtaining of the standard-mixed fuel flame-imaging data in the step S7 is completed, the controller 11 lets the standard-mixed fuel supply device 5 stop supplying the standard-mixed fuel N2, and lets the air supply device 6 stop supplying the air A.

Subsequently, the controller 11 lets the processing storage device 8 determine whether the test fuel flame-imaging data obtained in the step S3 corresponds to the standard-mixed fuel flame-imaging data obtained in the step S7 (step S8).

Specifically, the processing storage device 8 obtains, for example, a correlation function from the test fuel flame-imaging data and the standard-mixed fuel flame-imaging data. The processing storage device 8 determines that the test fuel flame-imaging data and the standard-mixed fuel flame-imaging data correspond to each other, when the value of the correlation function is included within a range stored beforehand (range in which a correlation coefficient is near 1). In addition, since the correlation function can be obtained based on the brightness data or the pattern data of the imaging data by using general-purpose software, the method to obtain the correlation function is well-known. Therefore, the description about the method to obtain the correlation function is omitted.

When it is determined that the images do not correspond to each other in the step S8, the controller 11 changes the ratio between normal heptane and isooctane in the standard-mixed fuel, the ratio stored in the processing storage device 8 (step S9).

A change quantity of the above ratio is set optionally. For example, the ratio between normal heptane and isooctane is changed so that the ratio of isooctane in the standard-mixed fuel rises by 1%.

After the step S9 is completed, the processing of the controller 11 returns to the step S5 and the control thereof is performed again.

In contrast, when it is determined that the images correspond to each other in the step S8, the controller 11 lets the processing storage device 8 determine that the octane number of the test fuel N1 is the octane number (the ratio of isooctane) of the standard-mixed fuel based on the standard-mixed fuel flame-imaging data corresponding to the test fuel flame-imaging data, and lets the processing storage device 8 output the octane number of the test fuel (step S10).

The controller 11 lets the output device 10 display the octane number of the test fuel N1 outputted from the processing storage device 8, and thereafter completes the operations.

As described above, in the fuel physical property determination method of this embodiment, in the steps S9 and S10, the octane number of the test fuel N1 is determined by comparing the test fuel flame-imaging data and the standard-mixed fuel flame-imaging data That is, in this embodiment, a physical property determination step in the present invention is constituted of the steps S9 and S10.

As described above, in the fuel physical property determination method of this embodiment, in the step S3, the imaging data is obtained by imaging flames formed by supplying the pre-mixed gas containing the test fuel N1 and the air A to the test tube 2. That is, in this embodiment, a test fuel flame-imaging step in the present invention is constituted of the step S3.

As described above, in the fuel physical property determination method of this embodiment, in the step S7, the imaging data is obtained by imaging flames formed by supplying the pre-mixed gas containing the standard-mixed fuel N2 and the air A to the test tube 2. That is, in this embodiment, a standard-mixed fuel flame-imaging step in the present invention is constituted of the step S7.

According to the fuel physical property determination device 1 and the fuel physical property determination method of this embodiment, the octane number of the test fuel is determined by comparing the imaging data (test fuel flame-imaging data) obtained by imaging flames formed using the test fuel N1 and the imaging data (standard-mixed fuel flame-imaging data) obtained by imaging flames formed using the standard-mixed fuel N2 having known physical properties.

Therefore, the octane number of the test fuel N1 can be determined without obtaining the temperature of the test tube 2. That is, according to the fuel physical property determination device 1 and the fuel physical property determination method of this embodiment, the octane number of the test fuel N1 can be determined without measuring the temperature gradient of the test tube 2, and it is possible to omit the steps to obtain the temperature gradient of the test tube 2, which cause an increase in work burden in conventional methods.

Consequently, according to the fuel physical property determination device 1 and the fuel physical property determination method of this embodiment, it is possible to shorten the time required to determine the octane number of the test fuel N1 by reducing the work burden thereof.

In the fuel physical property determination device 1 and the fuel physical property determination method of this embodiment, in the step S7, the standard-mixed fuel flame-imaging data is obtained by imaging flames formed by supplying the pre-mixed gas containing the standard-mixed fuel N2 and the air A to the test tube 2.

For example, the standard-mixed fuel flame-imaging data is obtained and is stored in the processing storage device 8 beforehand, and the octane number can be determined by comparing the standard-mixed fuel flame-imaging data stored beforehand and the test fuel flame-imaging data. In addition, in this case, it has to be secured that the environment in which the standard-mixed fuel flame-imaging data is obtained beforehand is the same as the environment in which the test fuel flame-imaging data is obtained, or data errors based on the difference between the obtaining environments have to be corrected.

In contrast, according to the fuel physical property determination device 1 and the fuel physical property determination method of this embodiment, in the step S7, the standard-mixed fuel flame-imaging data is obtained by imaging flames formed by supplying the pre-mixed gas containing the standard-mixed fuel N2 and the air A to the test tube 2. Therefore, the standard-mixed fuel flame-imaging data and the test fuel flame-imaging data can be obtained in the substantially same environment.

Consequently, according to the fuel physical property determination device 1 and the fuel physical property determination method of this embodiment, the octane number of the test fuel N1 can be determined more accurately.

In the fuel physical property determination device 1 and the fuel physical property determination method of this embodiment, as shown in the steps S5 to S9, the standard-mixed fuel flame-imaging data is obtained while changing the composition of the standard-mixed fuel (ratio between normal heptane and isooctane) until the test fuel flame-imaging data and the standard-mixed fuel flame-imaging data correspond to each other, and the octane number of the test fuel N1 is determined to be the octane number of the standard-mixed fuel based on the standard-mixed fuel flame-imaging data corresponding to the test fuel flame-imaging data.

Therefore, the octane number of the test fuel N1 can be determined more accurately, by controlling the change rate of the ratio between normal heptane and isooctane.

In the fuel physical property determination device 1 and the fuel physical property determination method of this embodiment, both of the area in which cold flames are expected to be generated and the area in which hot flames are expected to be generated are imaged.

Therefore, the octane number of the test fuel N1 can be determined based on the generation or non-generation of the cold and hot flames in addition to the generation position of flames. Consequently, the octane number of the test fuel N1 can be determined more accurately.

In the fuel physical property determination device 1 and the fuel physical property determination method of this embodiment, it is determined that the test fuel flame-imaging data and the standard-mixed fuel flame-imaging data correspond (or similar) to each other, by obtaining the correlation function from the test fuel flame-imaging data and the standard-mixed fuel flame-imaging data.

In addition, it does not have to be determined that the test fuel flame-imaging data and the standard-mixed fuel flame-imaging data correspond to each other, by always obtaining the correlation function.

For example, if fuels having the same octane number are burned in the same condition, the generation positions of cold flames and hot flames (that is, ignition temperatures) become the same. Therefore, when comparing the test fuel flame-imaging data and the standard-mixed fuel flame-imaging data, it is possible to determine whether the octane numbers are the same, for example, by extracting the data denoting the generation position of at least one of the cold and hot flames, from the test fuel flame-imaging data and the standard-mixed fuel flame-imaging data.

In addition, even in these cases, the generation positions of the cold and hot flames (that is, ignition temperatures) do not have to be concretely obtained as absolute value. The octane number can be determined by obtaining the generation positions as relative value in the test fuel flame-imaging data and the standard-mixed fuel flame-imaging data.

In other words, if fuels having the same octane number are burned in the same condition, the generation positions of cold flames and hot flames (that is, ignition temperatures) become the same, and the brightness distributions or the pattern distributions in the test fuel flame-imaging data and the standard-mixed fuel flame-imaging data are the same. Therefore, when the correlation coefficient of the correlation function obtained from the test fuel flame-imaging data and the standard-mixed fuel flame-imaging data is included within the range near 1, and the two-imaging data sets corresponding or being similar to each other, it can be considered that the octane numbers are the same (or similar to each other).

In addition, it may be determined that the test fuel flame-imaging data and the standard-mixed fuel flame-imaging data correspond to each other, based not only on the generation positions of the cold and hot flames (that is, ignition temperatures), but also on the calorific values of the cold and hot flames, the ratio between the calorific values, or the like. In this case, the brightness values of the imaging data of the flames become larger in accordance with the calorific values becoming larger, and the determination becomes easy.

In the fuel physical property determination device 1 and the fuel physical property determination method of this embodiment, the diameter of the internal flow path of the test tube 2 is set smaller than the flame-quenching distance at normal temperature. However, the present invention is not limited to this configuration, and it is possible to use a test tube having a diameter of the internal flow path thereof larger than the flame-quenching distance at normal temperature, as the test tube 2.

Second Embodiment

Next, a second embodiment of the present invention is described below. In the description of this second embodiment, the recitations about the same portions as that of the first embodiment are omitted or simplified.

Figure 3:
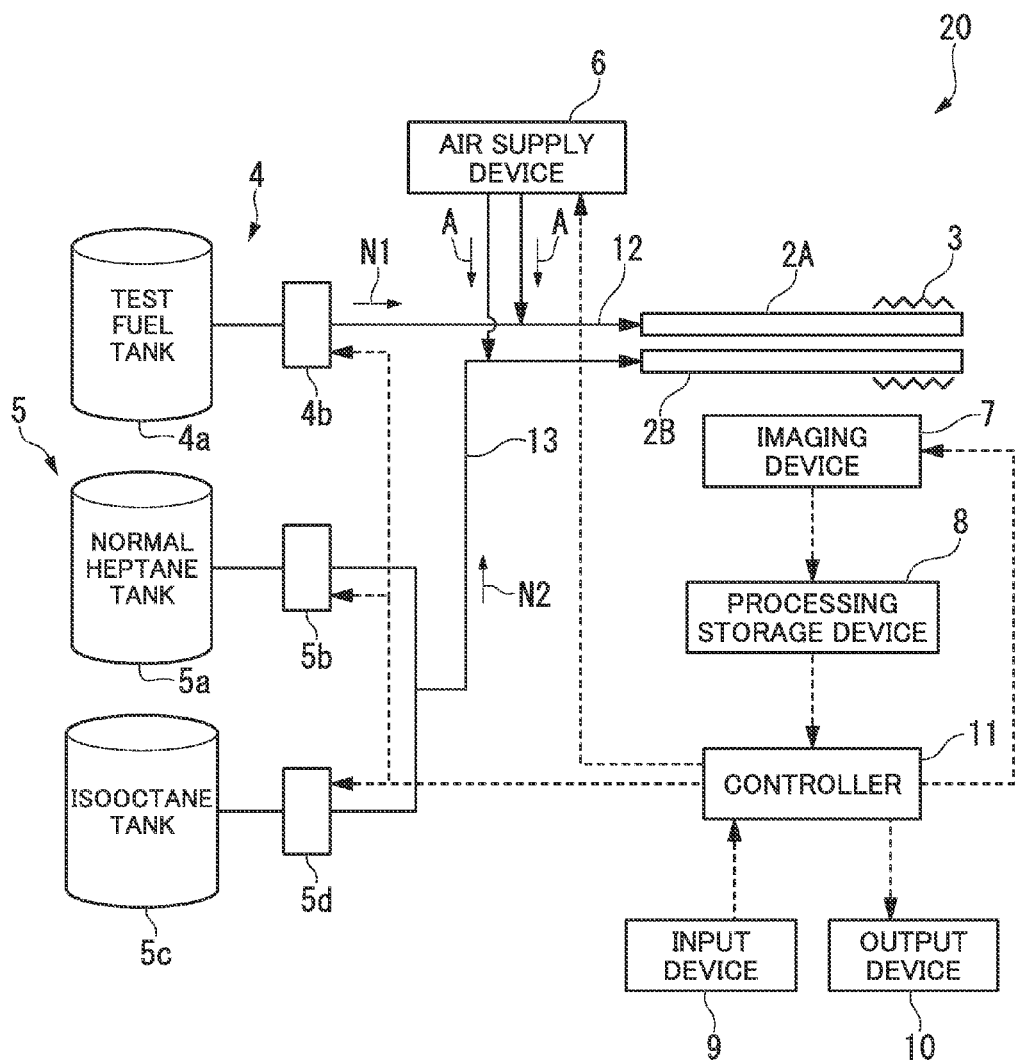
FIG. 3 is a schematic configuration diagram of a fuel physical property determination device in a second embodiment of the present invention.

FIG. 3 is a schematic configuration diagram of a fuel physical property determination device 20 in this embodiment. As shown in FIG. 3, the fuel physical property determination device 20 in this embodiment includes two test tubes 2A, 2B (first test tube and second test tube). The test tubes 2A, 2B are disposed next to each other in the direction orthogonal to the imaging direction of the imaging device 7 so that the imaging device 7 can image them together at the same time.

In the fuel physical property determination device 20 in this embodiment, the pre-mixed gas supply pipe 12 is connected to only one test tube 2A, whereby the test fuel supply device 4 is connected to only the test tube 2A. The standard-mixed fuel supply pipe 13 is directly connected to only the other test tube 2B, whereby the standard-mixed fuel supply device 5 is connected to only the test tube 2B.

The air supply device 6 is connected to each of the pre-mixed gas supply pipe 12 and the standard-mixed fuel supply pipe 13 so as to supply the air A to each. That is, in this embodiment, the pre-mixed gas supply pipe 12 becomes a flow path for the pre-mixed gas containing the test fuel N1, and the standard-mixed fuel supply pipe 13 becomes a flow path for the pre-mixed gas containing the standard fuel N2.

The heater 3 heats the test tubes 2A, 2B, and is disposed so as to surround the end portions of the test tubes 2A, 2B opposite to the end portions thereof to which the pre-mixed gases are supplied. The heater 3 is disposed at the position capable of forming the same temperature distribution in the test tubes 2A, 2B at the same time.

Figure 4:
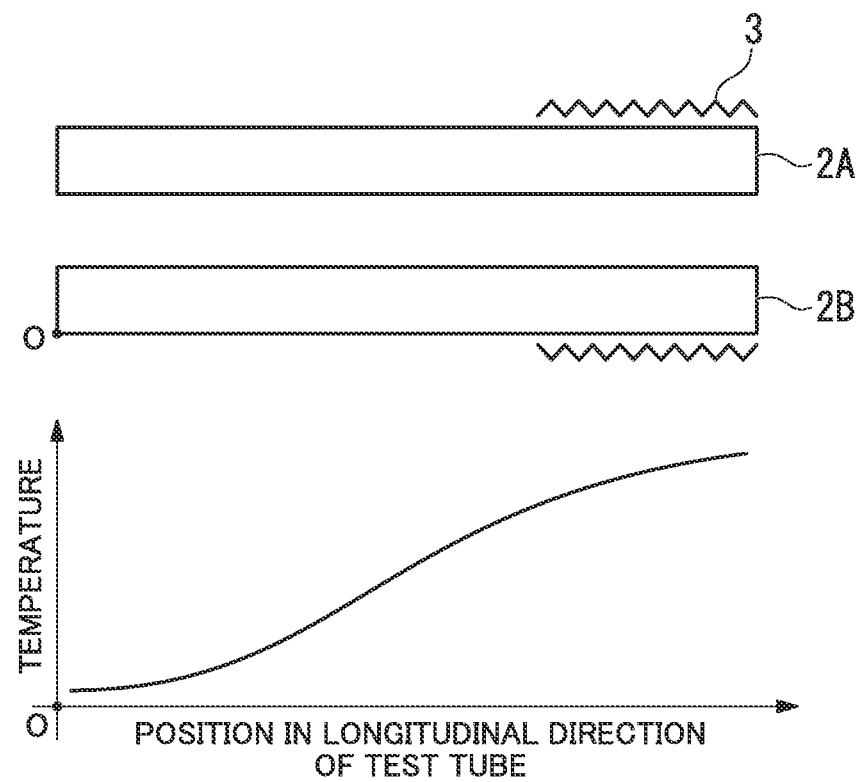
FIG. 4 is a graph showing the variation in temperatures applied to a test tube included in the fuel physical property determination device in the second embodiment of the present invention.

The heater 3 is disposed and heats both of the test tubes 2A, 2B at the same time, and thereby as shown in FIG. 4, the temperatures of the test tubes 2A, 2B similarly rise so as to be higher as approaching the heater 3 (a temperature distribution-forming step). That is, the same temperature distribution can be formed in the test tubes 2A, 2B.

In the fuel physical property determination device 20 of this embodiment having the above-described configuration, the pre-mixed gas containing the test fuel N1 and the air A is supplied to one test tube 2A of the disposed test tubes 2A, 2B, thereby forming flames, the pre-mixed gas containing the standard-mixed fuel N2 and the air A is supplied to the other test tube 2B, thereby forming flames, and imaging data is obtained by imaging a plurality of flames at the same time. At this time, the test tubes 2A, 2B in which the heater 3 surrounds the end portions thereof are heated for the same time, and have the same temperature distribution. Therefore, under the same temperature condition, it is possible to image the flames formed using the test fuel N1 and the air A, and the flames formed using the standard-mixed fuel N2 and the air A, at the same time.

Consequently, the flames by using the test fuel N1 and the air A, and the flames by using the standard-mixed fuel N2 and the air A can be formed in the same condition, and the octane number of the test fuel N1 can be determined more accurately.

Two test tubes or more to which the standard fuel is supplied may be provided, and thereby three test tubes or more may be provided. In this case, the ratios between normal heptane and isooctane become different to each other in the test tubes to which the standard fuel is supplied, and the octane number of the test fuel N1 can be determined in a shorter time.

It is also possible to heat test tubes to which the test fuel or the standard fuel is supplied, by supplying temperature control gas to around the test tubes in the longitudinal direction thereof. Therefore, the same temperature gradient (temperature distribution) can be formed in the test tubes.

Hereinbefore, preferable embodiments of the present invention are described with reference to the drawings, but the present invention is not limited to the above-described embodiments. A shape, a combination or the like of each constituent member shown in the above embodiments is illustrative only, and various modifications can be adopted based on a design request or the like within the scope not departing from the gist of the present invention.

For example, in the above embodiments, it is described that the octane number as a physical property of a test fuel is determined.

However, the present invention is not limited to this, and can be applied to a case of determining the cetane number as a physical property of a test fuel. The inventor performed experiments using the method and device in the present invention, and confirmed that the generation positions of flames (including cold flames and hot flames) inside a test tube are changed depending on fuels having various cetane numbers. That is, it is found that the cetane number of a test fuel can be determined by using the method and device in the present invention. In this case, operations can be performed by reading the octane number as the cetane number, in the above embodiments.

In addition, if the generation positions of flames depend on generation characteristics of harmful substances from a test fuel, the generation characteristics of harmful substances as physical properties of the test fuel can be also determined.

In the above embodiments, the flames in the test tube 2 are imaged in a stable state without the flames vibrating.

However, the present invention is not limited to this. It is also possible to image the flames in the test tube 2 in they vibrating, and to determine the physical properties of a test fuel by comparing the imaging data.

In the above embodiments, since the flames together with the test tube 2 are imaged, the data denoting the test tube 2 is included in the test fuel flame-imaging data and the standard-mixed fuel flame-imaging data.

Therefore, test tube-imaging data may be stored by imaging the test tube 2 to which a temperature gradient is applied, before the flames are formed, and the test tube-imaging data may be excluded from the test fuel flame-imaging data and the standard-mixed fuel flame-imaging data.

Thereby, the test tube-imaging data is eliminated from the test fuel flame-imaging data and the standard-mixed fuel flame-imaging data. Since only the data denoting the flames can be compared, the physical properties of a test fuel can be determined more exactly.

In the above embodiments, it is described that the heater has a cylindrical shape.

However, the fuel physical property determination method and device of the present invention are not limited to this. If a temperature gradient is formed in a test tube and the same temperature distribution is formed in test tubes, a heater may have a rectangular or elliptical cross-sectional shape.

In the above embodiments, the configuration of using air as an oxidant agent in the present invention is described.

However, the present invention is not limited to this, and other gas can be used as the oxidant agent.

In the above embodiments, the configuration in which the steps S1 to S10 are performed by the controller 11 is described.

However, the fuel physical property determination method of the present invention is not limited to this, and an operator may perform part or all of the steps S1 to S10.

In the above embodiments, every time the standard-mixed fuel flame-imaging data is obtained in the step S7, the judgment as to whether the test fuel flame-imaging data and the standard-mixed fuel flame-imaging data correspond to each other is performed (step S8).

However, the present invention is not limited to this. Standard-mixed fuel flame-imaging data sets may be obtained by imaging flames formed using standard-mixed fuels having various ratios between normal heptane and isooctane, and the standard-mixed fuel flame-imaging data sets and the test fuel flame-imaging data set may be compared.

In this case, it is possible to determine that the octane number of the test fuel is the octane number based on the standard-mixed fuel flame-imaging data set being the closest to the test fuel flame-imaging data set.

In addition to the method of determining that the octane number of the test fuel is the octane number based on the closest standard-mixed fuel flame-imaging data set, the method may be used in which the comparison is performed after interpolating the standard-mixed fuel flame-imaging data sets.

In a state in which the test fuel flame-imaging data and the standard-mixed fuel flame-imaging data correspond to each other, a case in which they completely correspond to each other is included, and a case in which they correspond to each other in a permitted scope in advance is also included.

For example, if the sizes or the directions in the test fuel flame-imaging data and the standard-mixed fuel flame-imaging data are different from each other, these imaging data sets can be compared. That is, even if one of them includes images obtained by imaging flames in expansion, in a case in which cold flames and hot flames are included in the scope of both imaging data sets and their positional relationships are obtained, the imaging data sets can be compared.

In the above embodiments, the imaging device 7 may image flames via a mirror or a prism.

Since the light emitted from the flames is guided via the mirror or the prism, the imaging device 7 can be disposed at an optional position. Therefore, for example, it is possible to store the test tube 2 in a pressure chamber having a window, and to dispose the imaging device 7 in the outside of the chamber.

INDUSTRIAL APPLICABILITY

According to the present invention, the physical properties of a test fuel can be determined without obtaining the temperature of a test tube. That is, according to the present invention, since the physical properties of the test fuel can be determined without measuring the temperature gradient of the test tube, it is possible to omit the steps to obtain the temperature gradient of the test tube, which cause an increase in work burden. As a result, it is possible to shorten the time required to determine the physical properties of the fuel, by reducing the work burden.

DESCRIPTION OF REFERENCE SIGNS 1, 20 Fuel physical property determination device
2, 2A, 2B Test tube
3 Heater
4 Test fuel supply device
5 Standard-mixed fuel supply device
6 Air supply device
7 Imaging device (imaging means)
8 Processing storage device (processing storage means)
9 Input device
10 Output device
11 Controller
N1 Test fuel
N2 Standard-mixed fuel
A Air (oxidant agent)

What is claimed is:

1. A fuel physical property determination method to determine a physical property of a test fuel, the method comprising:
a test fuel flame-imaging step of obtaining first imaging data by imaging flames formed inside a test tube by supplying a pre-mixed gas containing the test fuel and an oxidant agent, to the test tube which includes an internal flow path and in which a temperature distribution is formed; and
a physical property determination step of determining the physical property of the test fuel by comparing the first imaging data obtained in the test fuel flame-imaging step and second imaging data obtained by imaging flames ignited inside the test tube by supplying a pre-mixed gas containing a standard-mixed fuel and an oxidant agent, to the test tube, the standard-mixed fuel having a known physical property,
wherein the internal flow path of the test tube has a diameter set to be smaller than a flame-quenching distance at normal temperature, and
in the physical property determination step, data denoting a generation position of the flames in the first imaging data and data denoting a generation position of the flames in the second imaging data are used when the first and second imaging data are compared.

2. The fuel physical property determination method according to claim 1, further comprising
a standard-mixed fuel flame-imaging step of obtaining the second imaging data by imaging flames formed inside the test tube by supplying the pre-mixed gas containing the standard-mixed fuel and the oxidant agent, to the test tube.

3. The fuel physical property determination method according to claim 2,
wherein the standard-mixed fuel flame-imaging step is performed while changing a composition of the standard-mixed fuel, until the first imaging data obtained in the test fuel flame-imaging step and the second imaging data obtained in the standard-mixed fuel flame-imaging step correspond to each other, and
in the physical property determination step, the physical property of the test fuel is determined to be the physical property of the standard-mixed fuel based on the second imaging data corresponding to the first imaging data.

4. The fuel physical property determination method according to claim 2,
wherein the pre-mixed gas containing the test fuel and the oxidant agent is supplied to one of disposed test tubes, thereby forming flames,
the pre-mixed gas containing the standard-mixed fuel and the oxidant agent is supplied to the other of the test tubes, thereby forming flames, and
the first and second imaging data are obtained by imaging a plurality of flames at the same time.

5. The fuel physical property determination method according to claim 4, further comprising
a temperature distribution-forming step of forming the same temperature distribution in the test tubes,
wherein the first and second imaging data of the plurality of flames are obtained in a condition in which temperature distributions in the test tubes are the same in a longitudinal direction thereof.

6. The fuel physical property determination method according to claim 1,
wherein both of an area in which cold flames are expected to be generated and an area in which hot flames are expected to be generated are imaged.

7. The fuel physical property determination method according to claim 1,
wherein the physical property is an octane number.

8. The fuel physical property determination method according to claim 1,
wherein the physical property is a cetane number.

9. The fuel physical property determination method according to claim 1,
wherein the test tube has the temperature distribution in which the temperature of the test tube gradually increases in a longitudinal direction of the test tube.

10. A fuel physical property determination device to determine a physical property of a test fuel, the device comprising:
a test tube including an internal flow path;
a temperature distribution-forming device to form a temperature distribution in the test tube;
a supply device to supply a first pre-mixed gas containing the test fuel and an oxidant agent, to the test tube;
an imaging device to obtain first imaging data by imaging flames formed inside the test tube by supplying the first pre-mixed gas to the test tube; and
a processing storage device to determine the physical property of the test fuel by comparing the first imaging data obtained by the imaging device and second imaging data obtained by imaging flames formed inside the test tube by supplying a second pre-mixed gas containing a standard-mixed fuel and an oxidant agent, to the test tube, the standard-mixed fuel having a known physical property,
wherein the internal flow path of the test tube has a diameter set to be smaller than a flame-quenching distance at normal temperature, and
the processing storage device is configured to use data denoting a generation position of the flames in the first imaging data and data denoting a generation position of the flames in the second imaging data when the first and second imaging data are compared.

11. The fuel physical property determination device according to claim 10,
wherein the imaging device is configured to obtain the second imaging data by imaging flames formed inside the test tube by supplying the second pre-mixed gas containing the standard-mixed fuel and the oxidant agent, to the test tube.

12. The fuel physical property determination device according to claim 11,
wherein the imaging device is configured to repeatedly obtain the first and second imaging data, until the first and second imaging data correspond to each other, and
the processing storage device is configured to change a composition of the standard-mixed fuel, and to determine that the physical property of the test fuel is the physical property of the standard-mixed fuel when the first and second imaging data correspond to each other.

13. The fuel physical property determination device according to claim 11,
wherein the test tube includes a first test tube and a second test tube, and
the imaging device is configured to obtain the first imaging data by imaging flames formed by supplying the first pre-mixed gas to the first test tube, and to obtain the second imaging data by imaging flames formed by supplying the second pre-mixed gas to the second test tube.

14. The fuel physical property determination device according to claim 13,
wherein the temperature distribution-forming device is disposed so that temperature distributions in the first and second test tubes are the same in a longitudinal direction thereof.

15. The fuel physical property determination device according to claim 10,
wherein the imaging device is configured to obtain imaging data so as to include both of a first area in which cold flames are expected to be generated and a second area in which hot flames are expected to be generated.

16. The fuel physical property determination device according to claim 10,
wherein the physical property is an octane number.

17. The fuel physical property determination device according to claim 10,
wherein the physical property is a cetane number.

18. The fuel physical property determination device according to claim 10,
wherein the temperature distribution-forming device forms the temperature distribution in which the temperature of the test tube gradually increases in a longitudinal direction of the test tube.

* * * * *